(12) United States Patent
Behnke, II et al.

(10) Patent No.: US 9,192,424 B2
(45) Date of Patent: Nov. 24, 2015

(54) AC ACTIVE LOAD

(75) Inventors: Robert J. Behnke, II, Erie, CO (US);
Peter L. Valentyik, Boulder, CO (US);
Christopher J. Hahn, Longmont, CO (US)

(73) Assignee: Covidien LP, Mansfield, MA (US)

( * ) Notice: Subject to any disclaimer, the term of this patent is extended or adjusted under 35 U.S.C. 154(b) by 674 days.

(21) Appl. No.: 13/485,083

(22) Filed: May 31, 2012

(65) Prior Publication Data
US 2013/0325380 A1 Dec. 5, 2013

(51) Int. Cl.
*G01R 27/08* (2006.01)
*G06F 17/40* (2006.01)
(Continued)

(52) U.S. Cl.
CPC ............ *A61B 18/1233* (2013.01); *G01R 27/28* (2013.01); *G01R 31/42* (2013.01);
(Continued)

(58) Field of Classification Search
CPC .................. A61B 17/00; A61B 18/00; A61B 2018/00571; A61B 2018/00577; A61B 2018/00589; A61B 2018/00595; A61B 2018/00601; A61B 2018/00607; A61B 2018/00613; A61B 2018/00619; A61B 2018/00625; A61B 2018/0063; A61B 2018/00636; A61B 2018/00696; A61B 2018/00702; A61B 2018/00775; A61B 2018/00767; A61B 2018/773; A61B 2018/00779; A61B 2018/00827; A61B 2018/00833; A61B 2018/00875; A61B 2018/00892; A61B 2018/00988; A61N 1/00; A61N 1/18; A61N 1/32; G01D 7/00; G01D 9/00; G01D 21/00; G01R 19/00; G01R 27/00; G01R 27/02; G01R 27/08; G05B 9/00; G05B 9/02; G05B 11/00; G05B 11/01; G05B 15/00; G05B 15/02; G06F 11/00; G06F 11/30; G06F 11/32; G06F 11/34; G06F 15/00; G06F 15/16; G06F 17/00; G06F 17/10; G06F 17/40; G06F 19/00

USPC .............. 73/1.01, 1.88, 118.01, 432.1, 865.8, 73/865.9, 866.3; 322/7, 14, 17, 22, 23, 24, 322/25, 27, 28, 36, 37, 99, 100; 323/234, 323/265, 282, 285; 324/73.1, 500, 537, 324/600, 602, 750.01; 327/524, 574, 581; 338/13; 606/1, 32, 34, 37, 38, 39, 40, 606/41, 49; 607/1, 2, 59, 115, 116; 700/1, 700/28, 90, 286; 702/1, 57, 64, 65, 85, 127, 702/182, 187, 189; 708/100, 105, 200
See application file for complete search history.

(56) References Cited

U.S. PATENT DOCUMENTS 3,082,374 A * 3/1963 Buuck ........................... 324/73.1
3,601,126 A 8/1971 Estes
(Continued)

FOREIGN PATENT DOCUMENTS

DE 179607 3/1905
DE 1099658 2/1961
(Continued)

OTHER PUBLICATIONS

U.S. Appl. No. 10/406,690, filed Apr. 3, 2003, Robert J. Behnke, II.
(Continued)

*Primary Examiner* — Edward Cosimano

(57) ABSTRACT

An AC active load device for use with a generator and a controller to supply a variable impedance when supplied with an AC waveform. The AC active load device uses a transformer and one or more transistors to generate an average max load impedance greater than 1000 ohms over varying voltage levels. The transistor functions as a dynamically-controlled resistor to the generator when the generator supplies the AC voltage to the transformer. The transistors may be GaN FETs or LDMOSFETs. The transformer steps down a voltage supplied by a generator to a voltage below the threshold voltage of the transistors. A control voltage is supplied to the gate of the transistors and may be controlled by a controller. A voltage and current are outputted to the controller from the AC active load device. The AC active load device may be used to calibrate the generator.

20 Claims, 5 Drawing Sheets

(51) Int. Cl.
    *G06F 19/00* (2011.01)
    *A61B 18/12* (2006.01)
    *G01R 27/28* (2006.01)
    *G01R 31/42* (2006.01)
    *A61B 18/00* (2006.01)

(52) U.S. Cl.
    CPC ............ *A61B2018/0063* (2013.01); *A61B 2018/00595* (2013.01); *A61B 2018/00702* (2013.01); *A61B 2018/00779* (2013.01); *A61B 2018/00875* (2013.01); *A61B 2018/00988* (2013.01); *G06F 17/40* (2013.01); *G06F 19/00* (2013.01)

(56) References Cited

U.S. PATENT DOCUMENTS

| | | | |
|---|---|---|---|
| 3,897,788 | A | 8/1975 | Newton |
| 4,092,986 | A | 6/1978 | Schneiderman |
| 4,569,345 | A | 2/1986 | Manes |
| 4,634,958 | A * | 1/1987 | Cornwell ............... 323/255 |
| 5,559,688 | A | 9/1996 | Pringle |
| 5,789,907 | A * | 8/1998 | Casagrande ............ 323/335 |
| 5,830,212 | A | 11/1998 | Cartmell et al. |
| 6,923,804 | B2 | 8/2005 | Eggers et al. |
| D574,323 | S | 8/2008 | Waaler |
| 7,443,232 | B2 * | 10/2008 | Bladh ..................... 327/581 |
| 2006/0091869 | A1 * | 5/2006 | Zhang .................... 323/282 |
| 2007/0063746 | A1 * | 3/2007 | Bladh .................... 327/109 |
| 2012/0239020 | A1 | 9/2012 | Cunningham |
| 2012/0239025 | A1 | 9/2012 | Smith |
| 2012/0239026 | A1 | 9/2012 | Orszulak |
| 2012/0253342 | A1 | 10/2012 | Jensen |
| 2012/0265194 | A1 | 10/2012 | Podhajsky |
| 2012/0265195 | A1 | 10/2012 | Gilbert |
| 2012/0283731 | A1 | 11/2012 | Unger |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4206433 | 9/1993 |
| DE | 4339049 | 5/1995 |
| DE | 19506363 | 8/1996 |
| DE | 19717411 | 11/1998 |
| DE | 19848540 | 5/2000 |
| DE | 10 2008058737 | 4/2010 |
| EP | 246350 | 11/1987 |
| EP | 267403 | 5/1988 |
| EP | 296777 | 12/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 882955 | 12/1998 |
| EP | 1051948 | 11/2000 |
| EP | 1366724 | 1/2006 |
| EP | 880220 | 6/2006 |
| EP | 1776929 | 4/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| JP | 63 005876 | 1/1988 |
| JP | 2002-065690 | 3/2002 |
| SU | 166452 | 1/1965 |
| SU | 727201 | 4/1980 |
| WO | WO02/11634 | 2/2002 |
| WO | WO02/45589 | 6/2002 |
| WO | WO03/090635 | 11/2003 |
| WO | WO2006/050888 | 5/2006 |
| WO | WO2008/053532 | 5/2008 |

OTHER PUBLICATIONS

U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 13/118,973, filed May 31, 2011, James H. Orszulak.
U.S. Appl. No. 13/186,092, filed Jul. 19, 2011, George J. Collins.
U.S. Appl. No. 13/186,107, filed Jul. 19, 2011, George J. Collins.
U.S. Appl. No. 13/186,121, filed Jul. 19, 2011, George J. Collins.
U.S. Appl. No. 13/195,607, filed Aug. 1, 2011, James H. Orszulak.
U.S. Appl. No. 13/221,424, filed Aug. 30, 2011, James E. Krapohl.
U.S. Appl. No. 13/228,996, filed Sep. 9, 2011, Robert B. Smith.
U.S. Appl. No. 13/236,997, filed Sep. 20, 2011, Robert J. Behnke, II.
U.S. Appl. No. 13/237,068, filed Sep. 20, 2011, Robert J. Behnke, II.
U.S. Appl. No. 13/237,187, filed Sep. 20, 2011, Robert J. Behnke, II.
U.S. Appl. No. 13/237,342, filed Sep. 20, 2011, Robert J. Behnke, II.
U.S. Appl. No. 13/237,488, filed Sep. 20, 2011, Robert J. Behnke, II.
U.S. Appl. No. 13/247,043, filed Sep. 28, 2011, Donald W. Heckel.
U.S. Appl. No. 13/358,129, filed Jan. 25, 2012, Joseph D. Brannan.
U.S. Appl. No. 13/360,140, filed Jan. 27, 2012, James E. Krapohl.
U.S. Appl. No. 13/426,204, filed Mar. 21, 2012, Robert B. Smith.
U.S. Appl. No. 13/427,111, filed Mar. 22, 2012, Daniel A. Joseph.
U.S. Appl. No. 13/442,460, filed Apr. 9, 2012, James E. Krapohl.
U.S. Appl. No. 13/446,096, filed Apr. 13, 2012, James H. Orszulak.
U.S. Appl. No. 13/469,960, filed May 11, 2012, Robert J. Behnke, II.
U.S. Appl. No. 13/485,083, filed May 31, 2012, Robert J. Behnke, II.
U.S. Appl. No. 13/540,347, filed Jul. 2, 2012, Ronald J. Podhajsky.
U.S. Appl. No. 13/593,550, filed Aug. 24, 2012, Ronald J. Podhajsky.
U.S. Appl. No. 13/584,192, filed Aug. 13, 2012, Joseph D. Brannan.
U.S. Appl. No. 13/587,400, filed Aug. 16, 2012, James H. Orszulak.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.

(56) References Cited

OTHER PUBLICATIONS

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Zlatanovic M., "Sensors in Diffusion Plasma Processing" Microelectronics 1995; Proceedings 1995; 20$^{th}$ International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . " Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001494.9 dated Aug. 25, 2010.
International Search Report EP 07001494.9 extended dated Mar. 7, 2011.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
International Search Report EP09004250.8 dated Aug. 2, 2010.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP09763515.5 dated Nov. 29, 2011.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report EP10171787.4 dated Nov. 18, 2010.
International Search Report EP10172636.2 dated Dec. 6, 2010.
International Search Report EP10174476.1 dated Nov. 12, 2010.
International Search Report EP10178287.8 dated Dec. 14, 2010.
International Search Report EP10179305.7 dated Aug. 23, 2011.
International Search Report EP10179321.4 dated Mar. 18, 2011.
International Search Report EP10179353.7 dated Dec. 21, 2010.
International Search Report EP10179363.6 dated Jan. 12, 2011.
International Search Report EP10180004.3 dated Jan. 5, 2011.
International Search Report EP10180964.8 dated Dec. 22, 2010.
International Search Report EP10180965.5 dated Jan. 26, 2011.
International Search Report EP10181018.2 dated Jan. 26, 2011.
International Search Report EP10181060.4 dated Jan. 26, 2011.
International Search Report EP10182003.3 dated Dec. 28, 2010.
International Search Report EP10182005.8 dated Jan. 5, 2011.
International Search Report EP10188190.2 dated Nov. 22, 2010.
International Search Report EP10191319.2 dated Feb. 22, 2011.
International Search Report EP10195393.3 dated Apr. 11, 2011.
International Search Report EP11006233.8 dated Feb. 2, 2012.
International Search Report EP11155959.7 dated Jun. 30, 2011.
International Search Report EP11155960.5 dated Jun. 10, 2011.
International Search Report EP11168660 dated Sep. 28, 2011.
International Search Report EP11170959.8 dated Dec. 9, 2011.
International Search Report EP11173562.7 dated Nov. 24, 2011.
International Search Report EP11182150.0 dated Nov. 17, 2011.
International Search Report EP11188798.0 dated Dec. 27, 2011.

(56) References Cited

OTHER PUBLICATIONS

International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.

* cited by examiner

AC ACTIVE LOAD

TECHNICAL FIELD

The present disclosure is directed to electrosurgery and, in particular, to a system and method for electrosurgical generator power measurement. More specifically, to an AC active load.

BACKGROUND OF RELATED ART

Electrosurgical generators are employed by surgeons in conjunction with an electrosurgical instrument to cut, coagulate, desiccate and/or seal patient tissue. High frequency electrical energy, e.g., radio frequency (RF) energy, is produced by the electrosurgical generator and applied to the tissue by an electrosurgical tool. Both monopolar and bipolar configurations are commonly used during electrosurgical procedures.

Electrosurgical techniques and instruments can be used to coagulate small diameter blood vessels or to seal large diameter vessels or tissue, e.g., veins and/or soft tissue structures, such as lung, and intestine. A surgeon can cauterize, coagulate/desiccate and/or simply reduce or slow bleeding, by controlling the intensity, frequency and duration of the electrosurgical energy applied between the electrodes and through the tissue. For the purposes herein, the term "cauterization" is defined as the use of heat to destroy tissue (also called "diathermy" or "electro-diathermy"). The term "coagulation" is defined as a process of desiccating tissue wherein the tissue cells are ruptured and dried.

"Vessel sealing" or "tissue fusion" is defined as the process of liquefying the collagen and elastin in the tissue so that it reforms into a fused mass with significantly-reduced demarcation between the opposing tissue structures (opposing walls of the lumen). Coagulation of small vessels is usually sufficient to permanently close them while larger vessels or tissue need to be sealed to assure permanent closure. It has been known that different waveforms of electrosurgical energy are suited for different surgical affects, e.g., cutting, coagulation, sealing, blend, etc. For example, the "cutting" mode typically entails generating a continuous sinusoidal waveform in the frequency range of 250 kHz to 4 MHz with a crest factor in the range of 1.4 to 2.0. The "blend" mode typically entails generating a periodic burst waveform with a duty cycle in the range of 25% to 75% and a crest factor in the range of 2.0 to 5.0. The "coagulate" mode typically entails generating a periodic burst waveform with a duty cycle of approximately 10% or less and a crest factor in the range of 5.0 to 12.0. In order to effectively and consistently seal vessels or tissue, a pulse-like waveform is desired.

In order to optimize sealing or tissue fusion without causing unwanted charring of tissue at the surgical site or possibly causing collateral damage to adjacent tissue, e.g., thermal spread, it is necessary to accurately control the output from the electrosurgical generator, e.g., power, waveform, voltage, current, pulse rate, etc. It follows that accurate measurement of the output power of an electrosurgical generator greatly benefits the design, manufacture, and use thereof.

The task of acquiring power data from an electrosurgical generator unit typically involves coupling the RF output of the generator to a dummy load, and manually activating an output power mode and/or level via front panel controls or other actuator. The current value through the load is measured with an RMS voltmeter and recorded manually for each data point along a test sequence. Every data point must then be transferred into a form suitable for design analysis or individual product calibration by a design engineer or line technician. The entire series of measurements may be repeated for different power levels and with different dummy loads. For example, test data may be manually input into a spreadsheet or bench test equipment to calculate load power for each data point. Each power level and mode setting requires at least 20 data points to define a curve with a meaningful level of detail. Typically, at least three power levels are used to define a particular mode. Thus, for each electrosurgical mode, at least 60 data points need to be collected. This means that for an electrosurgical generator that can operate in a cut mode, a blend mode, a coagulation mode, and a sealing mode, 240 data points are required to meet the minimum level of precision required. The result is a time-consuming and labor-intensive product development cycle or manufacturing process which adds considerable cost to the product and negatively impacts time-to-market and margins.

Additionally, most active loads are designed for use with DC outputs. Typical DC active loads use a MOSFET. However, an AC waveform can damage the MOSFET because of the parasitic of the device and the intrinsic body diode. To accommodate the AC waveform, different configurations have been used such as an N-channel and a P-channel device (See FIG. 2B), or a common source configuration. However, in these configurations the device does not behave correctly over the waveform cycle. Further, the drain to source capacitance changes as the drain voltage varies, which induces load variations dependent on the output voltage level. Another approach for an active load to handle the AC waveform was to rectify the voltage into a DC voltage; however this results in unwanted spikes in the waveform as the diodes go through reverse recovery.

SUMMARY

It is an object of the present disclosure to provide an AC active load. More specifically, to an AC active load that can maintain an average max load impedance greater than 1000 ohms over varying voltage levels and frequencies. Further, using an AC active load to vary the resistance (impedance) provides more speed and repeatability over conventional load resistor testing.

According to an aspect of the present disclosure, an AC active load device is disclosed for use with a generator and a controller to supply a variable impedance when supplied with an AC waveform. The AC active load device uses a transformer and one or more transistors to generate an average max load impedance greater than 1000 ohms over varying voltage levels. The transistor functions as a dynamically-controlled resistor to the generator when the generator supplies the AC voltage to the transformer. The transistors may be GaN FETs or LDMOSFETs. The transformer steps down a voltage supplied by a generator to a voltage below the threshold voltage of the transistors. A control voltage is supplied to the gate of the transistors and may be controlled by a controller. A voltage and current are outputted to the controller. The AC active load device may be used to calibrate the generator.

According to another aspect of the present disclosure, an AC active load device includes a transformer configured to step down an AC voltage supplied by a generator and a control voltage supply. The AC active load device further includes a first transistor connected to the control voltage and the transformer. The first transistor functions as a dynamically-controlled resistor to the generator when the generator supplies the AC voltage to the transformer.

According to a further aspect of the present disclosure, the first transistor may generate a voltage drop. The AC active load device may be connected to a controller through a voltage sensor that outputs the voltage drop and a current sensor that outputs a current, and the controller is configured to receive the current and voltage from the voltage and current sensors. Further, the controller may be configured to dynamically control the first transistor by varying a voltage supplied by the control voltage supply. The controller may be configured to vary the voltage supplied by the control voltage supply to provide a constant voltage across the AC active load device, a constant current across the AC active load device, a constant power across the AC active load device, or a constant impedance across the AC active load device.

According to a further aspect of the present disclosure, the first transistor may be a GaN FET or a LDMOS FET.

According to another aspect of the present disclosure, the control voltage may be connected between a first resistor and a second resistor and a gate of the first transistor and a gate of a second transistor.

According to a further aspect of the present disclosure, the transformer may be connected to a drain of the first transistor.

According to another aspect of the present disclosure, the transformer may be connected to a plurality of diodes and to a source of the first transistor via a first resistor.

According to a further aspect of the present disclosure, the active load device may supply an average max load impedance greater than 1000 ohms over varying voltage levels and/or frequencies.

According to another aspect of the present disclosure, a system includes a generator configured to supply an AC voltage to a transformer within an AC active load device. The system further includes a controller configured to control an AC active load device by varying a voltage supplied by a control voltage. A first transistor within the AC active load device functions as a dynamically-controlled resistor. The controller is further configured to receive a voltage and current from the AC active load, and in response to the received current or voltage adjust one or more parameters of the generator.

According to a further aspect of the present disclosure, the first transistor may be a GaN FET or a LDMOS FET.

According to another aspect of the present disclosure, the AC active load device may be a stands alone device. Alternatively, the AC active load device may be part of the generator, which allows for self-calibration.

According to a further aspect of the present disclosure, the AC Active load device may be part of the generator and may provide for self calibration with the controller configured to communicate with the generator to verify or calibrate one or more sensors of the generator across varying impedance and power levels.

According to another aspect of the present disclosure, the controller may be configured to vary the control voltage to allow for a constant voltage mode, a constant current mode, a constant power mode, a constant impedance mode, a closed loop mode, or a fully automated mode.

According to another aspect of the present disclosure, a method for measuring the performance of an electrosurgical generator. The method includes the step of providing a series of parameters defining a test sequence, the parameters including an impedance and a power level. The method further includes the step of electrically coupling the output of an electrosurgical generator to an AC active load device having the capability to present a variable impedance to the output of the electrosurgical generator. The AC active load device includes a transformer and a transistor. The method further includes the steps of activating an electrosurgical generator in accordance with a parameter of the test sequence, and measuring the output of the electrosurgical generator. Also, the method includes the steps of computing an impedance value based upon the output of the electrosurgical generator, and comparing the computed impedance value to the impedance parameter of the test sequence to determine an active load control signal. Additionally, the method includes the step of driving the AC active load device in accordance with the active load control signal to generate an impedance in accordance with the test sequence.

The method may further include the step of recording the measured output of the electrosurgical generator.

Alternatively or in addition, the method may include the step of comparing the computed impedance to the impedance parameter of the test sequence to derive an error signal.

Alternatively or in addition, the method may include the steps of providing the error signal and a test parameter as inputs to a proportional-integral-derivative controller, and computing an active load control signal with the proportional-integral-derivative controller.

Alternatively or in addition, the method may include the step of acquiring the series of parameters defining a test sequence from a host configuration module.

Alternatively or in addition, the method may include the steps of calculating a calibration parameter in accordance with the error signal, relaying the calibration parameter to the electrosurgical generator, and storing the calibration parameter in the electrosurgical generator.

BRIEF DESCRIPTION OF THE DRAWINGS

Various embodiments of the subject instrument are described herein with reference to the drawings wherein.

DETAILED DESCRIPTION

Figure 1:
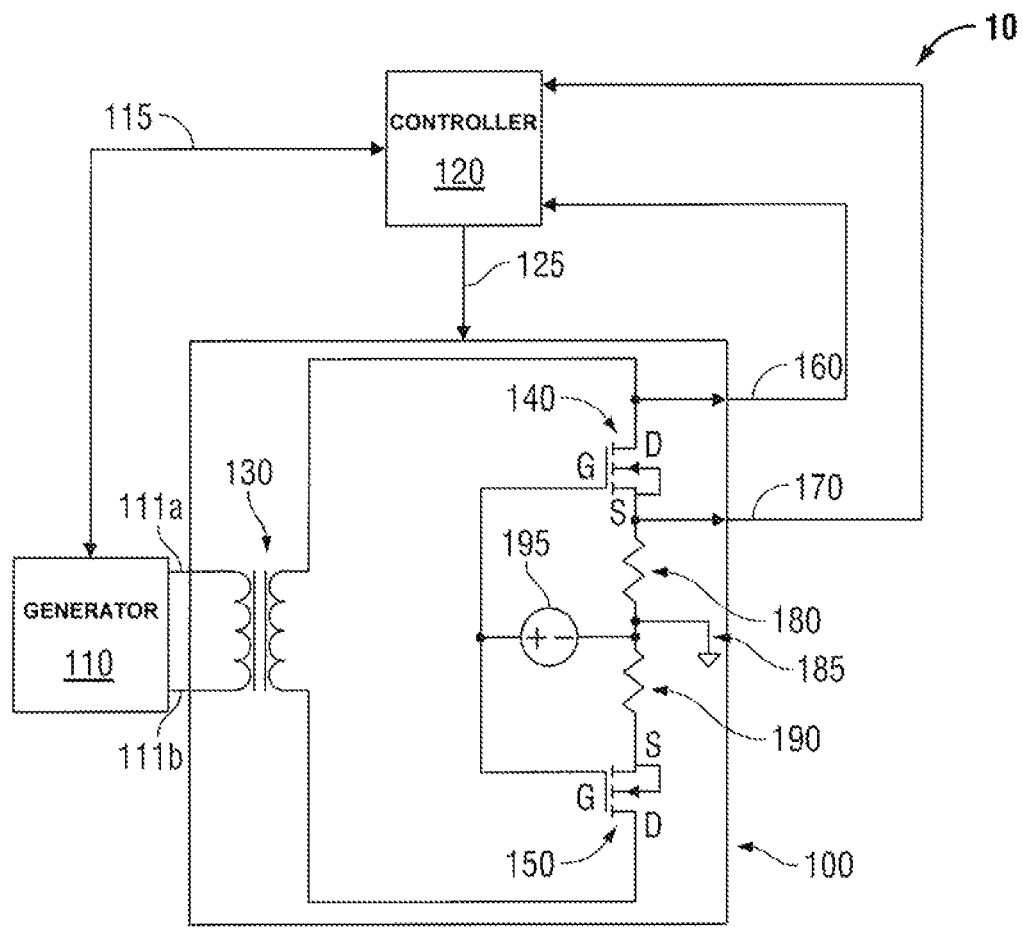
FIG. 1 is a schematic diagram of an embodiment of an active load device in accordance with the present disclosure.

Particular embodiments of the present disclosure are described hereinbelow with reference to the accompanying drawings; however, it is to be understood that the disclosed embodiments are merely examples of the disclosure, which may be embodied in various forms. The terminology used herein is for the purpose of describing particular embodiments only, and is not intended to be limiting Well-known and/or repetitive functions and constructions are not described in detail to avoid obscuring the present disclosure in unnecessary or redundant detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. It is to be understood that embodiments in accordance with the present disclosure may be practiced in any orientation without limitation. In this description, as well as in the drawings, like-referenced numbers represent elements which may perform the same, similar, or equivalent functions.

Referring to FIG. 1, a system 10 of using an AC active load 100. AC active load device 100 has the capability to present a variable load (e.g., variable impedance) to an alternating-current generator 110 such as, without limitation, those commonly employed in electrosurgery. In this manner, a drive signal presented to the AC Active load 100 establishes a variable load that simulates a tissue load.

The AC active load 100 is connected to outputs 111a and 111b of generator 110 and controller 120. The AC active load 100 may be a stand alone unit, within a surgical instrument (not shown), or within the generator. As a stand alone unit, the AC active load 100 may be used to test different generators. When the AC active load 100 is located within a generator 110, then the AC active load 100 may be used for self-calibration. The AC active load 100 is dynamically controlled by the controller 120 to provide large range of impedances to the generator 110 including arcing of the generator 110.

The AC active load 100 includes a first and second transistor 140, 150 respectively. The transistors may be a gallium nitride (GaN) field effect transistor (FET) or a laterally diffused metal oxide semiconductor (LDMOS) FET. GaN and LDMOS FETs are configured to withstand high frequencies, however one drawback to GaN and LDMOS FETs is that they have a relatively low drain voltage. Both the GaN and LDMOS FET have a threshold maximum voltage of about 100 V. In contrast, a MOSFET has a threshold voltage around 1200 V.

The AC active load 100 includes a transformer 130. The transformer 130 receives the AC voltage from the generator 110 and steps down the AC voltage to under the maximum voltage of the transistor 140, 150. The transformer 130 is connected to a drain on both the first and second transistors 140, 150. In selecting an appropriate transformer, the transformer is selected to minimize high frequency losses, such as reverse recovery in the rectifying diodes.

A control voltage 195 is supplied to a gate on both the first and second transistors 140, 150. The control voltage 195 may supply a set voltage or may be controlled by the controller 120 via connection 125.

A first and second resistor 180, 190 are connected between a source on both the first and second transistors 140, 150 and a ground 185. The resistors 180, 190 increase the control voltage 195 range that may be supplied to the gate of both the first and second transistors 140, 150. The resistor may range in size from about 0.1 ohms to about 5 ohms Further, the resistors 140, 150 decrease the possibility transistors 140, 150 "running away". Run away occurs when the temperature of a transistor increases, the voltage drop tends to go down, and the transistor becomes even more conductive thereby allowing more current to pass resulting in the transistor stops functioning. Additionally, the first and second resistors 180, 190 control when the AC active load 100 turns on by providing negative feedback to the AC active load 100, and will maintain a more constant current flow through the AC active load 100.

By connecting the first and second transistors 140, 150 in a back-to-back configuration as shown in FIG. 1 a constant load is produced over the entire waveform of the AC voltage received through transformer 130. Alternatively, other configurations may be possible that provide a constant load over the entire AC waveform and do not have high frequency losses. The proper designed AC active load limits high frequency losses, has load consistency over an entire AC waveform, and can simulate a desired impedance equivalent to simulating a tissue load or for a changing load profile.

A first output 160 connected to the drain of transistor 140 supplies a voltage to controller 120 or other similar device. A second output 170 connected to the source of the transistor 140 supplies a current to controller 120 or other similar device.

The controller 120 may adjust the control voltage 195 based on the supplied voltage and/or current into the AC active load 100. For a constant voltage mode, the controller 120 may vary resistance of the AC active load 100 to keep a constant voltage across the AC active load 100. For a constant current mode, the controller 120 may vary resistance of the AC active load 100 to keep a constant current through the AC active load 100. For a constant power mode, the controller 120 may multiply the current and voltage together to produce a power signal for controlling the resistance across the AC active load 100. For a constant impedance mode, the controller 120 may divide the voltage by the current to produce an impedance signal for controlling the resistance across the AC active load 100. Additionally, the controller may adjust the control voltage 195 to control the AC active load in any two or more modes at the same time. The controller 120 may also include memory (not shown) that may include load curves for testing the generator 110.

Alternatively, the AC active load 100 may be used to close a loop between the generator 110 and the controller 120. For example, when a larger power is outputted from the generator 110, the impedance from the AC active load 100 would increase in response to the change in power from the generator 110.

In another alternative, the AC active load 100 may be used with the controller 120 to calibrate and/or for verification of the generator 110. One example is shown in pending U.S. patent application Ser. No. 13/049,459 entitled "SYSTEM AND METHOD FOR ELECTROSURGICAL GENERATOR POWER MANAGEMENT" filed on Mar. 16, 2011, the entire content of which is incorporated herein by reference. The controller 120 may be configured to communicate with the generator 110 via data bus 115 data collected from the AC active load 100. The data may be collected to verify or calibrate the generator's sensor (not shown) across impedance and power levels. If the AC active load 100 is internal to the generator 110, then the generator 110 could perform a self-calibration and sensor check, eliminating the need to send the generator 110 back for service. The self-calibration may be configured to be performed automatically during non-use or after a certain period of time. Alternatively, the self-calibration may be performed in response to a user command. Further, the controller may also use the AC active load for real-time measurement of electrical parameters while in service.

Figure 2A:
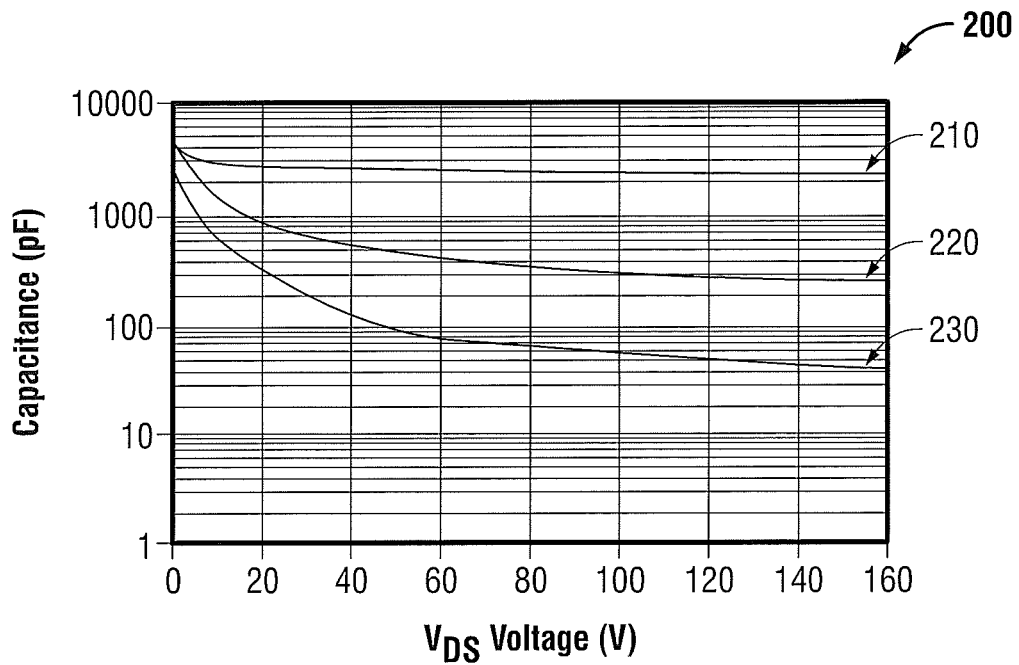
FIG. 2A is a plot of output capacitance with respect to drain voltage for a MOSFET device according to active load shown in FIG. 2B.
Figure 2B:
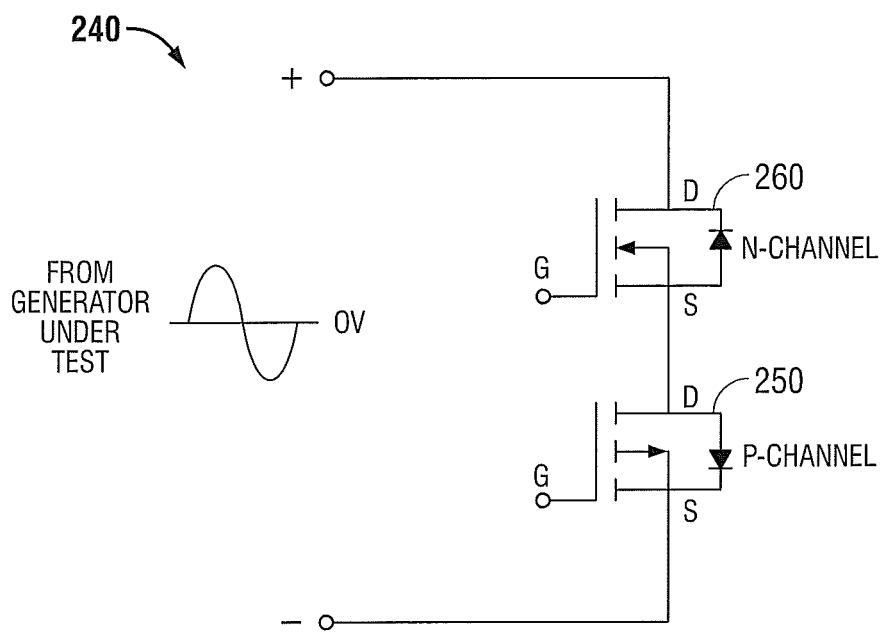
FIG. 2B is a schematic diagram of a prior art active load device.

Referring to FIG. 2A, plot 200 shows capacitance with respect to voltage for a prior art active load 240 (shown in FIG. 2B). Line 210 shows the input capacitance ($C_{iss}$), where the $C_{iss}$ is the equal to capacitance gate to source ($C_{gs}$). Line 220 shows the output capacitance ($C_{oss}$), where the $C_{oss}$ is equal to capacitance drain to source ($C_{ds}$). Line 230 sows the reverse transistor capacitance ($C_{rss}$), where the $C_{rss}$ is equal to capacitance gate to drain ($C_{gd}$). For an active load 240 having an n-channel MOSFET 260 and a p-channel MOSFET 250, a typical $C_{oss}$ starts around 4 nF and decays till about 100V and levels off at 200 pF. For example, when an AC waveform is 500 KHz, the estimated $C_{oss}$ is 2 nF at 10V, then the impedance is 160 ohms. While at 100V, the estimated $C_{oss}$ is 2 pF, then the impedance is 1600 ohms. This illustrates that a high impedance is difficult to achieve in low amplitude generator outputs. Further, when the AC waveform is sinusoidal, linear, or ramp, the impedance changes over the cycle of the waveform.

Figure 3:
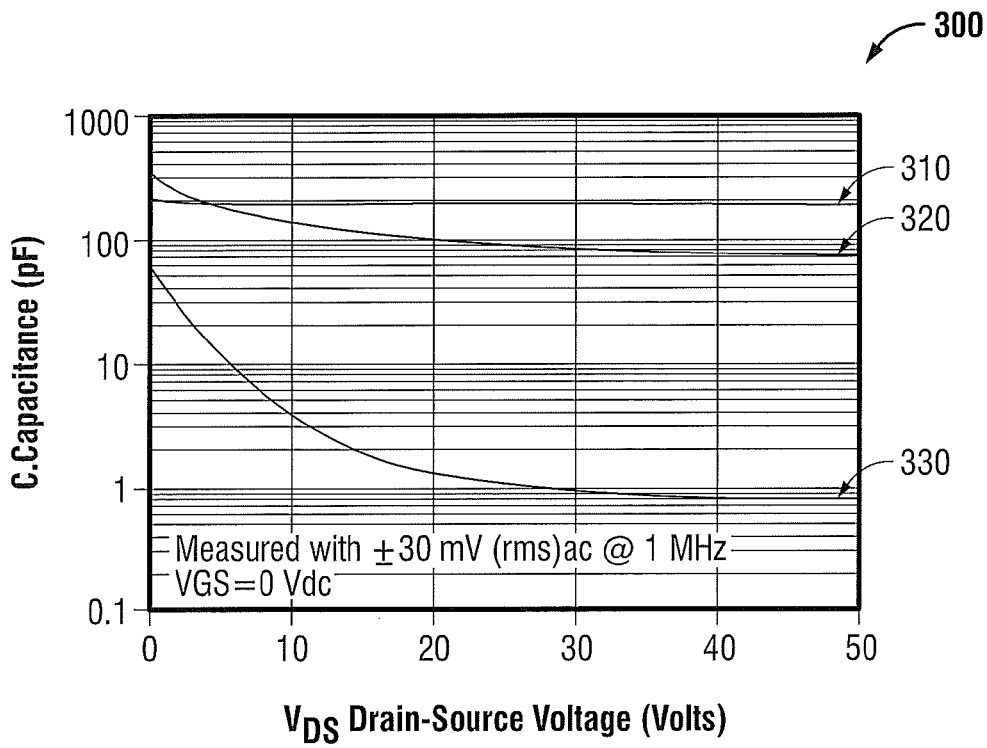
FIG. 3 is a plot of output capacitance with respect to drain voltage of a LDMOS FET device according to an embodiment of the present disclosure.
Figure 4:
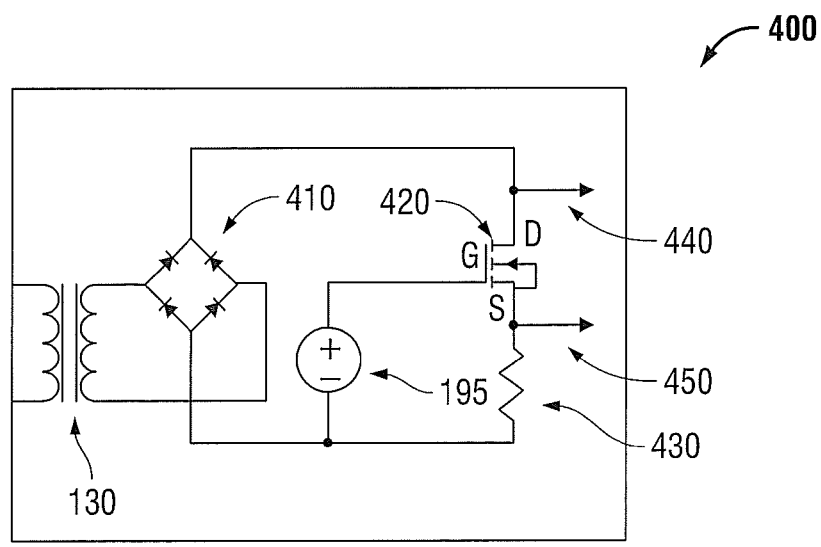
FIG. 4 is a schematic diagram of an alternative embodiment of an active load device in accordance with the present disclosure.

Referring to FIG. 3, plot 300 shows capacitance with respect to voltage for active load 100 (alternatively active load 400 shown FIG. 4 may be used). Line 310 shows the input capacitance ($C_{iss}$), where the $C_{iss}$ is the equal to capacitance gate to source ($C_{gs}$). Line 320 shows the output capacitance ($C_{oss}$), where the $C_{oss}$ is equal to capacitance drain to source ($C_{ds}$). Line 330 shows the reverse transistor capacitance ($C_{rss}$), where the $C_{rss}$ is equal to capacitance gate to drain ($C_{gd}$). For an active load 100, a typical $C_{oss}$ starts around 400 pF and decays till about 20V and levels off at 80 pF. For example, when an AC waveform is 500 KHz, the estimated $C_{oss}$ is 150 pF at 10V, then the impedance is over 2000 ohms. While at 100V, the estimated $C_{oss}$ is 80 pF, then the impedance is about 4000 ohms. This illustrates that a high (max) impedance (average above 1000 ohms) is easily achieved with the AC active load 100.

Referring to FIG. 4, an alternative AC active load 400 is shown. AC active load 400 includes transformer 130 and control voltage 195. The AC active load 400 includes four Schottky diodes in a diode bridge 410 configuration. The Schottky diodes may be silicon carbide diodes or other similar diodes that have no reverse recovery. The use of diodes without reverse recovery limits the high frequency losses. The diode bridge 400 is connected between the transformer 130 and a drain of transistor 420. The diode bridge 400 is further connected to the control voltage 195 via resistor 430 to the source of transistor 420. Similar to transistors 140, 150 in FIG. 1, transistor 420 may be GaN FET or LDMOS FET. A first output 440 connected to the drain of transistor 420 supplies a voltage to controller 120 or other similar device. A second output 450 connected to the source of the transistor 420 supplies a current to controller 120 or other similar device.

By connecting the first transistor 140 and the diode bridge together a constant load is produced over the entire waveform of the AC voltage received through transformer 130. Alternatively, other configurations may be possible that provide a constant load over the entire AC waveform and do not have high frequency losses. The proper designed AC active load limits high frequency losses, has load consistency over an entire AC waveform, and can simulate a desired impedance equivalent to simulating a tissue load or for a changing load profile.

Figure 5:
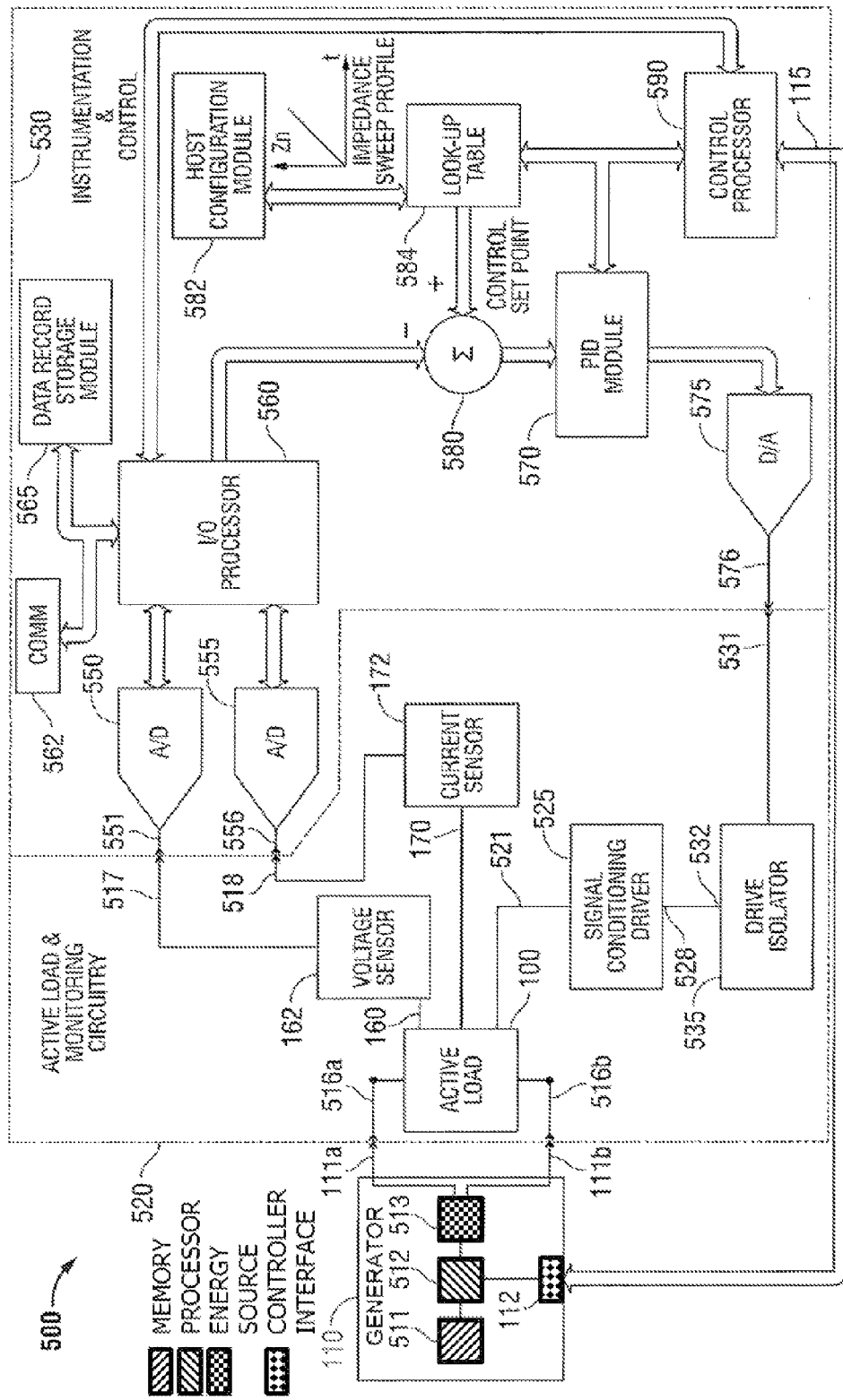
FIG. 5 is a functional block diagram of an embodiment of an electrosurgical power measurement system in accordance with the present disclosure.

Referring to FIG. 5, there is shown a block diagram of an embodiment an electrosurgical power measurement system 500. The disclosed system includes an AC active load section 520 operably coupled to an electrosurgical generator 110 and an instrumentation and control section 530. Electrosurgical generator 110 includes a controller interface 112 configured to facilitate the control of the various functions thereof, e.g., energy activation, energy deactivation, operational mode (cut, coagulate, blend, seal, etc.), output power, operating frequency, waveform, firmware update, calibration, and the like. Generator 110 includes a processor 512 adapted to communicate with controller interface 112 and programmed to manage the operational functions of generator 110 at least in accordance with a generator control signal received by controller interface 112. Processor 512 is operably coupled to memory 511 that may include operational software instructions executable by processor 512, calibration data, historical data, and test data. The contents of memory 511 may be modified in accordance with a signal received via controller interface 112. An energy source 513 having outputs 111a and 111b is configured to generate electrosurgical energy and is operably coupled to processor 512. Outputs 111a and 111b may be configured for monopolar or bipolar operation. Additional outputs may be configured in order to provide polyphase operation.

Active load section 520 is configured to receive an electrosurgical signal from electrosurgical generator 110, to present active load 100 to outputs 111a and 111b of electrosurgical generator 110, and to provide measurement signals to and receive drive signals from control section 530. A pair of inputs 516a and 516b is provided to receive electrosurgical energy from outputs 111a and 111b of electrosurgical generator 110 under test. A voltage sensor 162 is electrically connected to active load 100, more specifically to a drain of transistor 140. Voltage sensor 162 is configured to provide a voltage measurement signal at voltage measurement signal output 517. A current sensor 172 is electrically connected to active load 100, more specifically to a source of transistor 140 and is configured to provide a current measurement signal at current measurement signal output 518. Current and voltage sensing may be achieved using a non-contact method such as a voltage- and/or current-measuring transformer. In an embodiment, the active load device current and/or voltage measuring sensor (e.g., transformer) may provide a sensing output signal representative of, and/or proportional to, the corresponding measured current and/or voltage.

Active load section 520 further includes a drive isolator 535 having an input 531 configured to receive an active load drive signal from control section 530. Drive isolator 535 is further configured to provide galvanic isolation between active load section 520 and control section 530, and may include a photocoupling arrangement (e.g., an optoisolator), a transformer coupling arrangement, and/or a radio (RF) link arrangement.

An output 532 from drive isolator 535 is operably coupled to an input 528 of signal conditioning driver 525. Signal conditioning driver 525 buffers and/or amplifies the drive signal to provide a pair of control drive signals adapted to drive a balanced active load device 100. Signal conditioning driver 525 includes a control drive output 521 for controlling the control voltage 195.

Control section 530 includes a voltage sensor input 551, a current sensor input 556, an active load drive signal output 576, and a control signal output 115. Control section 530 includes a number of processing and/or storage modules that may be embodied in hardware, software, or a combination thereof. Voltage sensor input 551 is configured to receive a voltage sensor signal from voltage output 517 and couples the voltage sensor signal to an input of analog-to-digital (A/D) converter 550. Current sensor input 556 is configured to receive a current sensor signal from current output 518 and couples the current sensor signal to an input of analog-to-digital (A/D) converter 555. A/D converters 550, 555 are configured to convert the respective input signals thereof into digital form for use by input-output processor 560 as described in detail herein. A/D converters 550, 555 may be operated in a continuous sampling mode wherein the respective sensor signal is digitized at a sampling rate, which may range from about 5 MHz (e.g., five million samples per second) to about 40 MHz. A/D converters 550, 555 may additionally or alternatively be operated in a supervised mode wherein samples are digitized under control of input-output processor 560 or other control device. In embodiments, A/D converters 550, 555 may be operated in a windowed mode wherein a series of samples are collected for a predetermined period of time. A/D converters 550, 555 may utilize any suitable encoding scheme for digitally representing the respective analog sensor signals thereof, including without limitation, binary, two's complement, binary coded decimal (BCD).

An input-output processor 560 is in communication with A/D converters 550 and 555, data record storage unit 565, summation module 580 and control processor 590. Input-output processor 560 may include the capability of executing a set of program instructions for executing a method of electrosurgical generator power measurement as described herein. Input-output processor 560 is configured to receive voltage and current measurement data from A/D converters 550 and 555, respectively. During use, voltage and current measurement data received by input-output processor 560 is stored in data record module 565. Stored voltage and current measurement data may include set point data (e.g., the desired or intended output voltage and/or current) corresponding thereto, actual (measured) data, and error data (e.g., a difference between measured data and set point).

Host configuration module 582 includes a test parameter set, or test "profile", that describes a series of parameters defining a test sequence, such as without limitation, target load values, impedance values, and power levels, that simulate a tissue response typically seen during an electrosurgical procedure. A test profile may include a series of impedance targets expressed over a predetermined time period. Additionally or alternatively, a profile may include a power level, a voltage level, and/or a current level corresponding to a target impedance value. Host configuration module 582 may include one or more profiles that are selectively loadable into lookup table 584 for use. A profile may include target impedance values, target power levels, target voltage levels, target current levels, target reactance levels, and the like. In embodiments, the profile may be stored in a database, an indexed table, or other suitable data structure, and may be encoded using any suitable manner of encoding.

Instrumentation and control section 530 includes a control processor 590 that is in operative communication with input-output processor 560, lookup table 584, and proportional-integral-derivative (PID) module 570. Control processor 590 is configured to communicate with a generator 110 under test to, e.g., provide a control signal to generator 110 in accordance with a target value stored in lookup table 584. In embodiments, control processor 590 includes the capability to download calibration data that may include, without limitation, trim values, bias values, adjustments, offsets, and power parameters, to generator 110. Generator 110 may include the capability to commit calibration data to a calibration database (not explicitly shown) included within memory 511.

At the start of a measurement cycle, a desired profile that is stored in host configuration module 582 is loaded into lookup table 584 for use. Control processor 590 communicates an energy activation request to generator 110 via control signal output 115 in accordance with the loaded profile in lookup table 584. A target load value is obtained from lookup table 584 and applied as an initial setpoint value to PID module 570. Input-output processor 560 computes instantaneously generated power and impedance values from the measured current and voltage. The calculated impedance value is communicated from input-output processor 560 to summation module 580. Summation module 580 generates an error signal proportionate to an impedance control parameter set point provided by lookup table 584 and the instantaneous impedance calculated by input-output processor 560. The error signal is communicated to PID module 570, which, in turn, outputs a drive control signal to digital to analog (D/A) converter 575. D/A converter 575 includes an analog output 576 that is operably coupled to input 531 of drive isolator 530, which, in turn, drives active load device 100 via signal conditioning driver 525. A closed loop control circuit is thereby established wherein the target load setpoint obtained from lookup table 584 is compared to the calculated impedance value to maintain the desired active load presented to generator 110.

Actual measured voltage and current values are stored in data storage module 565 in association with the target setpoint values and/or calculated valued corresponding therewith, e.g., impedance, power, etc. In an embodiment, the values stored in data storage module 565 may be transmitted via a communication port 562 to another device, e.g., a personal computer, for further processing and/or analysis. Communication port 562 may include any suitable communication interface, including without limitation, a network interface (e.g., Ethernet), a wireless interface (e.g., a Bluetooth® wireless interface, an IEEE 802.11™ wireless interface, a Wi-Fi® wireless interface), a legacy interface (e.g., RS-232, EIA-485), a Universal Serial Bus (USB) interface, and the like.

A measurement cycle as described herein is performed iteratively for each control setpoint of the selected profile to establish an impedance sweep profile at one power level (e.g., seal intensity control level) of the generator 110 under test. Once a measured current and or control parameter reaches a steady state value listed in lookup table 584, or within a tolerance therefrom, control processor 590 communicates with input-output processor 560 to store the instantaneous values of current, voltage, computed power and impedance into data record storage module 565. This measurement cycle is repeated over the range of impedance values in the impedance sweep profile. The impedance sweep profile may also be represented by a curve fitting function. Over the simulated tissue impedance range, power curve performance parameters can be computed with respect to the power output set point of the generator 110 under test.

Figure 6:
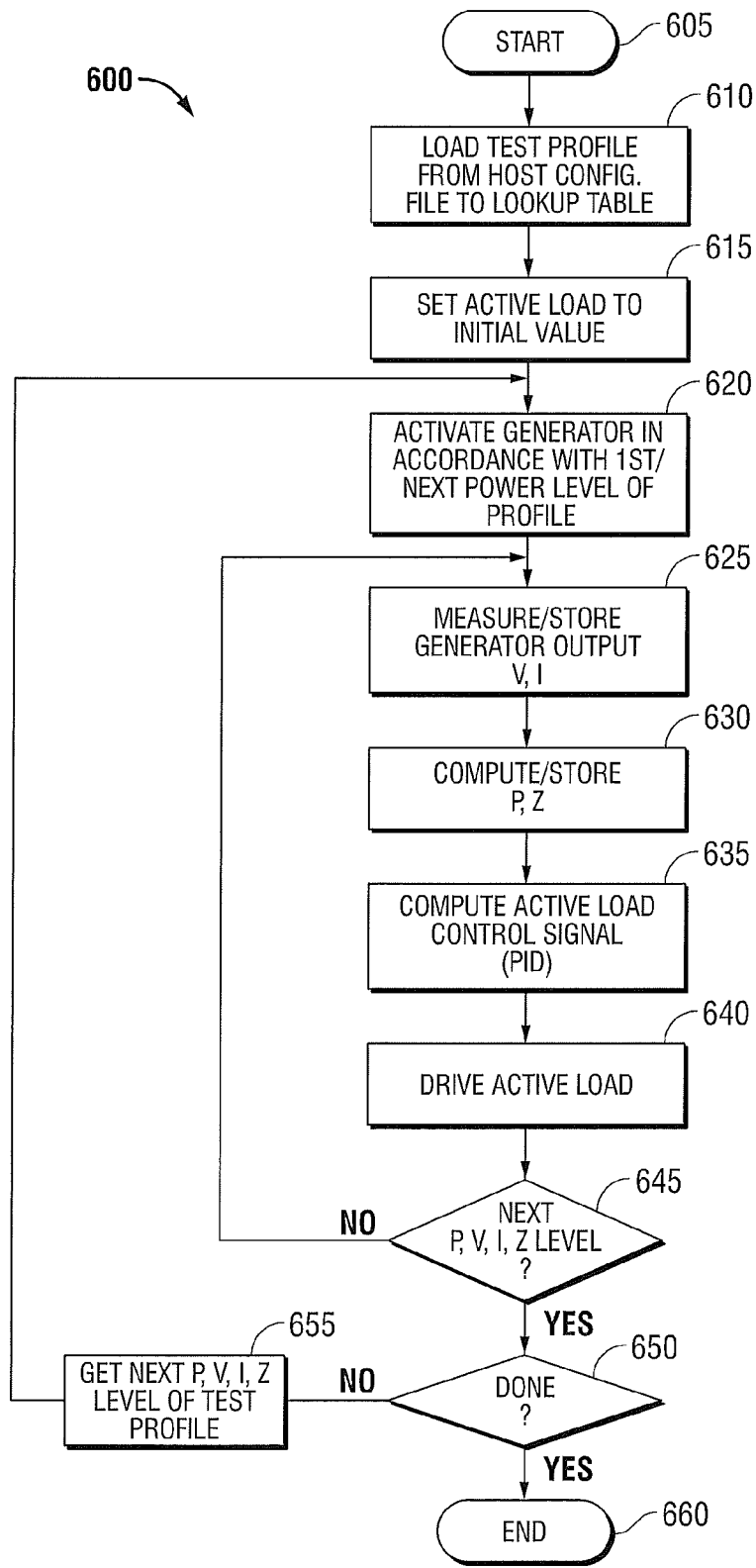
FIG. 6 is a flow chart of an embodiment of a method for electrosurgical generator measurement in accordance with the present invention.

A method 600 of performing electrosurgical measurement in accordance with the present disclosure is illustrated in FIG. 6. The method starts with an entry point 605 wherein various housekeeping and system initializations may be performed. For example, and without limitation, the various modules may perform a self-test, the various interfaces may confirm that proper electrical connections have been established with counterpart modules and/or components, and any hardware or software initializations required to achieve operational readiness are performed. In step 610, a desired test profile is loaded from a host configuration module to the lookup table for use. In step 615, an AC active load device 100 is set to an initial value that presents an initial load to the output of an electrosurgical generator under test, e.g., generator 110. In step 620, the generator 110 (under test) is activated in accordance with the first power level of the test profile, thereby delivering electrosurgical energy to the active load device 100. In step 625, voltage and current measurements are taken at the active load 100 and, optionally, the measured values are stored in a memory, e.g., data storage module 565. In step 630, power and impedance values are computed from the voltage and current measurements taken in step 625. Optionally, the computed power and impedance values are stored in a memory, e.g., data storage module 565.

In step 635, the active load control signal is computed by inputting the target (e.g., setpoint) impedance value of the current test profile step and the error (e.g., difference between setpoint impedance value and the computed impedance value) into a proportional-integral-derivative module, which, in turn, outputs an active load control signal. In step 640 the active load control signal is used to drive the active load device towards the desired, e.g., setpoint impedance value.

In the step 645 a determination is made whether the present measurement step is sufficiently stabilized to attain a valid reading, e.g., a verification that a power, voltage, current, and/or impedance value(s) (e.g., "P,V,I,Z") is found to be within a preset tolerance (e.g., +/−5%) for a preset number of consecutive measurement cycles (e.g., until a stable reading is obtained) and/or for a preset period of time (e.g., determined by a stable reading time period). If a determination is made that the reading(s) have not sufficiently stabilized, the present measurement cycle iterates to step 625, and processing proceeds from step 625 as described hereinabove. Conversely, if it is determined a valid reading has been acquired, the cycle iterates to step 650 wherein a determination is made whether the present test has been completed, e.g., all measurement steps in the present test profile have been performed. If a determination is made that the present test has not completed, the cycle iterates to step 655 wherein the next target power, voltage, current, and/or impedance setpoint is obtained from the lookup table, and processing proceeds from step 620 as described hereinabove. If, alternatively, in step 650 a determination is made that the present test is completed, the cycle concludes with an exit point at step 660.

The described embodiments of the present disclosure are intended to be illustrative rather than restrictive, and are not intended to represent every embodiment of the present disclosure. The steps of a method disclosed herein may be performed in a different order than that described, and/or the operations performed within an individual step or steps may be desirably be combined into a single step without departing from the scope and spirit of said method. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. An AC active load device, comprising:
   a transformer configured to step down an AC voltage supplied by a generator;
   a control voltage supply; and
   a first transistor connected to the control voltage and the transformer, wherein the first transistor functions as a dynamically-controlled resistor to the generator when the generator supplies the AC voltage to the transformer.

2. The AC active load device according to claim 1, wherein the first transistor is a GaN FET or a LDMOS FET.

3. The AC active load device according to claim 1, wherein the control voltage is connected between a first resistor and a second resistor and a gate of the first transistor and a gate of a second transistor.

4. The AC active load device according to claim 1, wherein the transformer is connected to a plurality of diodes and to a source of the first transistor via a first resistor.

5. The AC active load device according to claim 1, wherein the active load device supplies an average max load impedance greater than 1000 ohms.

6. The AC active load device according to claim 1, wherein the first transistor generates a voltage drop.

7. The AC active load device according to claim 6, wherein the AC active load is connected to a controller through a voltage sensor that outputs the voltage drop and a current sensor that outputs a current, and the controller is configured to receive the current and voltage from the voltage and current sensors.

8. The AC active load device according to claim 7, wherein the controller is configured to dynamically control the first transistor by varying a voltage supplied by the control voltage supply.

9. The AC active load device according to claim 8, wherein the controller can vary the voltage supplied by the control voltage supply to provide a constant voltage across the AC active load device, a constant current across the AC active load device, a constant power across the AC active load device, or a constant impedance across the AC active load device.

10. A system, comprising:
    a generator configured to supply an AC voltage to a transformer within an AC active load device;
    a controller configured to control an AC active load device by varying a voltage supplied by a control voltage, wherein a first transistor within the AC active load device functions as a dynamically-controlled resistor; and
    a controller configured to receive a voltage and current from the AC active load, and in response to the received current or voltage adjust one or more parameters of the generator.

11. The system according to claim 10, wherein the first transistor is a GaN FET or a LDMOS FET.

12. The system according to claim 10, wherein the AC active load device provides an average max load impedance greater than 1000 ohms.

13. The system according to claim 10, wherein the AC active load device is part of the generator and provides for self-calibration with the controller configured to communicate with the generator to verify or calibrate one or more sensors of the generator across varying impedance and power levels.

14. The system according to claim 10, wherein the controller is configured to vary the control voltage to allow for a constant voltage mode, a constant current mode, a constant power mode, a constant impedance mode, a closed loop mode, or a fully automated mode.

15. A method for measuring performance of an electrosurgical generator, comprising:
    providing a series of parameters defining a test sequence, the parameters selected from the group consisting of an impedance, a voltage, a current, and a power level;
    electrically coupling an output of an electrosurgical generator to an AC active load device having a capability to present a variable impedance to the output of the electrosurgical generator, wherein the AC active load device includes a transformer and a transistor;
    activating an electrosurgical generator in accordance with a parameter of the test sequence;
    measuring the output of the electrosurgical generator;
    computing an impedance value based upon the output of the electrosurgical generator;
    comparing the computed impedance value to an impedance parameter of the test sequence to determine an active load control signal; and
    driving the AC active load device in accordance with the active load control signal to generate an impedance in accordance with the test sequence.

16. The method according to claim 15, further comprising the step of recording the measured output of the electrosurgical generator.

17. The method according to claim 15, further comprising acquiring the series of parameters defining a test sequence from a host configuration module.

18. The method according to claim 15, further comprising:
calculating a calibration parameter in accordance with an error signal;
relaying the calibration parameter to the electrosurgical generator; and
storing the calibration parameter in the electrosurgical generator.

19. The method according to claim 15, further comprising comparing the computed impedance value to the impedance parameter of the test sequence to derive an error signal.

20. The method according to claim 19, further comprising:
providing the error signal and a test parameter as inputs to a proportional-integral-derivative controller; and
computing an active load control signal with the proportional-integral-derivative controller.

* * * * *